United States Patent
Drutz et al.

(10) Patent No.: US 6,423,694 B1
(45) Date of Patent: *Jul. 23, 2002

(54) METHOD OF TREATING OTITIS MEDIA WITH URIDINE TRIPHOSPHATES AND RELATED COMPOUNDS

(75) Inventors: David J. Drutz, Houston, TX (US); Janet L. Rideout, Raleigh; Karla M. Jacobus, Cary, both of NC (US)

(73) Assignee: Inspire Pharmaceuticals, Inc., Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/604,463

(22) Filed: Feb. 21, 1996

(51) Int. Cl.$^7$ .............................................. A61K 31/70
(52) U.S. Cl. .......................... 514/51; 514/47; 424/437; 424/465
(58) Field of Search ................................ 424/437, 465; 514/47, 51

(56) References Cited

U.S. PATENT DOCUMENTS

| | | | |
|---|---|---|---|
| 5,260,073 A | * 11/1993 | Phipps | 424/465 |
| 5,292,498 A | * 3/1994 | Boucher, Jr. | 424/45 |
| 5,420,116 A | * 5/1995 | Puchelle et al. | 514/47 |
| 5,635,160 A | * 6/1997 | Stutts et al. | 514/47 |
| 5,789,391 A | * 8/1998 | Jacobus et al. | 514/51 |
| 5,837,861 A | * 11/1998 | Pendergast et al. | 536/25.6 |
| 5,900,407 A | * 5/1999 | Yerxa et al. | 514/47 |
| 5,958,897 A | * 9/1999 | Jacobus et al. | 514/49 |
| 5,972,904 A | * 10/1999 | Jacobus et al. | 514/51 |
| 5,981,506 A | * 11/1999 | Jacobus et al. | 514/47 |

FOREIGN PATENT DOCUMENTS

| | | | |
|---|---|---|---|
| FR | 2677250 | * | 12/1992 |
| FR | 2684299 | * | 6/1993 |
| WO | 9211016 | * | 7/1992 |

OTHER PUBLICATIONS

McCraig et al., "Trends in Antimicrobial Drug Prescribing Among Office Based Physicians in the United States," *Journal of the American Medical Association,* 273(3), 214–219 (Jan. 18, 1995).††*

Klein, "Otitis Media," *Clinical Infectious Diseases,* 19, 823–833 (Nov., 1994). ††*

Schwartz et al., "Purulent Otitis Media in Adults," *Archives of Internal Medicine,* 152, 2301–2304 (Nov., 1992).††*

Teele et al., "Otitis Media in Infancy and Intellectual Ability, School Achievement, Speech and Language at Age 7 Years," *Journal of Infectious Diseases,* 162, 685–694 (Sep., 1990).Reference supplied by applicant.*

Wintermeyer et al., "Chronic Suppurative Otitis Media," *Annals of Pharmacotherapy,* 28, 1089–1099 (Sep., 1994), Reference supplied by applicant.*

Poole et al., "Otitis Media Complications and Treatment Failures: Implications of Pneumococcal Resistance," *Pediatric Infectious Disease Journal,* 14(4), S23–S26, (Apr., 1995), Refernece supplied by applicant.*

Grundfast, "Management of Otitis Media and the New Agency for Health Care Policy and Research Guidelines," *Archives Otolaryngol. Head Neck Surgery,* 120, 797–798 (Aug., 1994), Reference supplied by applicant.*

Gheber et al., "Extracellular ATP Binding Proteins as Potential Receptors in Mucociliary Epithelium: Characterization Using [$^{32}$P]3'–O–(4–Benzoyl)benzoyl ATP, a Photoaffinity Label," *Journal of Membrane Biology,* 147, 83–93 (1995), Reference supplied by applicant.*

Cusack et al., "Subtypes of P2–Purinoceptors—Studies Using Analogues of ATP," *Annals of the New York Academy Of Sciences,* 603, 172–181 (1991??), Reference supplied by applicant.*

Kenner et al., "Nucleotides. Part XXVIII. A Synthesis of Uridine–5' Triphosphate (UTP)," *Journal of the Chemical Society (GB),* 1954, 2288–2293, Reference supplied by applicant.*

Hall et al., "Nucleoside Polyphosphates. II. A Synthesis of Uridine–5'–di– and –Triphosphates," *Journal of the American Chemical Society,* 76, 5056–5059 (Oct. 20, 1954), Reference supplied by applicant.*

Budavari et al. (eds.), *The Merck Index,,* 11th Edition, Merck & Co., Inc., Rahway, NJ, 1989, pp. 1554–1555, see entry 9795 (UTP), Reference supplied by applicant.*

(List continued on next page.)

*Primary Examiner*—Gary Geist
*Assistant Examiner*—Lawrence E. Crane
(74) *Attorney, Agent, or Firm*—Albert P. Halluin; Robin C. Chiang; Howrey Simon Arnold & White, LLP

(57) ABSTRACT

A method of promoting drainage of congested middle ear fluid in a subject in need of such treatment is disclosed. The method comprises administering to the middle ear of the subject a uridine triphosphate such as uridine 5'-triphosphate (UTP), an analog of UTP, or any other analog, in an amount effective to promote drainage of congested middle ear fluid by hydrating mucous secretions in the middle ear or by stimulating ciliary beat frequency in the middle ear or eustachian tube. The method is useful for treating patients afflicted with otitis media and other middle ear diseases, otitis externa, and inner ear diseases including Ménière's Disease. Pharmaceutical formulations and methods of making the same are also disclosed. Methods of administering the same would include any liquid suspension (including nasal drops or spray), oral, inhaled by nebulization, topical, injected or suppository form.

8 Claims, No Drawings

OTHER PUBLICATIONS

Goody et al., "Thiophosphate ANalogs of Nucleoside Di– and Triphosphates," *Journal of the American Chemical Society*, 93(23), 6252–6257 (Nov. 17, 1971).*

Hoard et al., "Conversion of Mono– and Oligodeoxyribonucleotides to 5'–Triphosphates," *Journal of the American Chemical Society*, 87(8), 1785–1788 (Apr. 20, 1965), Reference supplied by applicant.*

Yoshikawa et al.(I), "A Novel Method for Phosphorylation of Nucleosides to 5'–Nucleotides," *Tetrahedron Letters*, 1967(50), 5065–5068, References supplied by applicant.*

Yoshikawa et al.(II), "Studies of Phosphorylation. III. Selective Phosphorylation of Unprotected Nucleosides," *Bulletin of the Chemical Society of Japan*, 42(12), 3505–3508 (Dec., 1969), Reference supplied by applicant.*

Moffatt et al., "Nucleoside Polyphosphates. X. The Synthesis and Some Reactions of Nucleoside–5' Phosphomorpholidates and Related Compounds. Improved Methods for the Preparations of Nucleoside–5' Polyphosphates," *Journal of the American Chemical Society*, 83, 649–659 (Feb. 5, 1961), Reference supplied by applicant.*

Fischer et al., "Identification of Potent, Selective $P_{2y}$–Purinoceptor Agonists: Structure–Activity Relationships for 2–Thioester Derivatives of Adenosine 5'–Triphosphate," *Journal of Medicinal Chemistry*, 36(24), 3937–3946 (1993).††*

Kochetkov et al., "New Reaction of Adenine and Cytosine Derivatives, Potentially Useful for Nucleic Acid Modification," *Tetrahedron Letters*, 1971(22), 1993–1996.††*

Barrio et al., "Fluorescent Adenosine and Cytidine Derivatives," *Biochemical and Biophsical Research Communications*, 46(2), 597–604 (1972).††*

Secrist III et al., "Fluorescent Modifications of Adenosine––Containing Coenzymes. Biological Activities and Spectroscopic Properties," *Biochemistry*, 11(19), 3499–3506 (1972).††*

Ciesiolka et al., "New Observations concerning the Chloroacetaldehyde Reaction with Some tRNA Constituents. Stable Intermediates, Kinetics and Selectivity of the Reaction," *Nucleic Acids Research*, 5(3), 789–804 (Mar. 3, 1978).††*

Kayasuga–Mikado et al., "Modification of Adenine and Cytosine Derivatives with Bromoacetaldehyde," *Chemical & Pharmaceutical Bulletin*, 28(3), 932–938 (1980).††*

Ludwig et al., "Rapid and Efficient Synthesis of Nucleoside 5'–O–(1–Thiotriphosphates), 5'–Triphosphates and 2', 3'–Cyclophosphorothioates Using 2–Chloro–4H–1, 3, 2–benzodioxaphosphorin–4–one," *Journal of Organic Chemistry*, 54(3), 631–635 (1989).††*

Blackburn et al., "The Synthesis and Metal Binding Characteristics of Novel Isopolar Phosphonate Analogues of Nucleotides," *Journal of the Chemical Society(GB)*, Perkin Transactions I, 1984, 1119–1125.††*

Myers et al., "Phosphonic Acid Analogs of Nucleoside Phosphates. I. The Synthesis of 5'–Adenylyl Methylenediphosphonate, a Phosphonic Acid Analog of ATP," *Journal of the AMerican Chemical Society*, 85, 3292–3295 (Oct. 20, 1963).††*

Rapaport et al., "HeLa Cell DNA Polymerase α Is Tightly Associated With Trytophanyl–tRNA Synthease and Diadenosine 5', 5'''–$P^1$, $P^4$–tetraphosphate Binding Activities," *Proceedings of the National Academy of Sciences (USA)*, 78(2), 838–842 (Feb., 1981).††*

Ng et al., "The Action of a Water–Soluble Carbodiimide on Adenosine–5'–polyphosphates," *Nucleic Acids Research*, 15(8), 3573–3580 (1987).*

Boucher et al., "Mechanisms and Therapeutic Actions of Uridine Triphosphate in the Lung,", Ch. 55 in "Adenosine and Adenine Nucleotides" From *Molecular Biology to Integrative Physiology*, Baladinelli et al. (eds), Aluwer Academic Publishers, Boston, MA, 1995, only pp. 525–532 supplied.*

Hoffman et al., "Catecholamines and Sympathomimetic Drugs," Chapter 10 in *Goodman and Gilman's The Pharmaceutical Basis of Therapeutics*, 8th Edition, Pergamon PRess, New York, NY, 1990, Gilman et al. (eds.), only pp. 214–217 supplied.*

Lethem et al., "Nucleotide Regulation of Goblet Cells in Human Airway Epithelial Explants: Normal Exocytosis in Cystic Fibrosis," *American Journal of Respiratory Cell Molecular Biology*, 9, 315–322 (1993).*

Mason et al., "Regulation of Transepithelial Ion Transport and Intracellular Calcium by Extracellular ATP in Human Noramal and Cystic Fibrosis Airway Epithelium," *Bristish Journal of Pharmacology*, 103, 1649–1656 (1991).*

Noone et al., "Effects on Cough Clearance by Aerosolized Uridine–5'–Trisphosphate ±Amiloride in Patients with Primary Ciliary Dyskenesia," *American Journal of Respiratory Critical Care Medicine*, 154, A530 (May 14, 1996); see Abstract at the top of column 1.*

Olivier et al., "Acute Safety and Effects on Mucocilliary Clearance of Aerosolized Uridine 5'–Triphosphate±Amiloride in Normal Healthy Adults," *American Journal of Respiratory Critical Care Medicine*, 154, 217–233 (1996).*

Berkov et al., *The Merck Manual of Diagnosis and Therapy*, 16th Edition, Merck & Co., Rahway, NJ, May, 1992, only pp. 666–667 supplied.*

Thomas (ed), *Taber's Cyclopedic Medical Dictionary*, 17th Edition, F.A. Davis Co., Philadelphia, PA, 1993, only pp. 1802–1804 supplied.*

Brown et al., "Evidence that UTP and ATP Regulate Phospholipase C Through a Common Extracellular 5'–Nucleotide Receptor In Human Airway Epithelial Cells," *Molecular Pharamcology*, 40, 648–655 (1991).*

Drutz et al., Uridine 5'–Triphosphate (UTP) Regulates Mucocilliary Clearance Via Purinergic Receptor Activity, (disclosed at the "Purines '96" meeting) *Drug Development Research*, 37(3), 185 (1996); see Abstract at bottom of column 1.*

Knowles et al., "Activation by Extracellular Nucleotides of Chloride Secretion in the Airway Epithelia of Patients with Cystic Fibrosis," *New England Journal of Medicine*, 325, 533–538 (Aug. 22, 1991).*

Lazarowski et al., "Pharmacological Selectivity of the Cloned Human $P_{2U}$Purinoceptor: Potent Activation by Diadenosine Tetraphosphate," *British Journal of Pharmacology*, 116, 1619–1627 (1995).*

L. McCraig and J. Hughes, *JAMA* 273(3), 214–19 (1995).

J. Klein, *Clin. Infect. Dis.* 19, 823–33 (1994).

L. Schwartz and R. Brown, *Arch Intern Med* 152, 2301–04 (1992).

D. Teele, et al., *J. Infect Dis* 1621, 6895–94 (1990).

S. Wintermeyer and M. Nahata, *Annals of Pharmacotherapy* 28, 1089–99 (1994).

M. Poole, *Pediatr Infect Dis J.* 14(4), 523–26 (1995).

K. Grundfast, *Arch Otolaryngol Head Neck Surg.* 120, 797–98 (1994).

R. Boucher, et al., Adenosine and Adenine Nucleotides: From Molecular Biology to Integrative Physiolog., p. 525–53 entitled, "Mechanisms and Therapeutic Actions of Uridine Triphosphates in the Lung" (L. Belardinelli, et al., ed., Alumwer Academic.

L. Gheber, et al., *J. Membrane Biol.* 147, 83–93 (1995).

N. Cusack and S. Hourani, *Annals N.Y. Acad. Sci.* 603, 172–81 (entitled Biological Actions of Extracellular ATP.

Kenner et al., *J. Chem. Soc.* 1954, 2288.

Hall & Khorana, *J. Am. Chem. Soc.* 76, 5056 (1954).

Merck Index, Monograph No. 9795 (11th Ed. 1989).

R.S. Goody and F. Eckstein, *J. Am. Chem. Soc.* 93, 6252 (1971).

D. Hoard and D. Ott, *J. Am. Chem. Soc.* 87, 1785–1788 (1965).

M. Yoshikawa, et al., *Tetrahedron Lett.* 5065–68 (1967) and *idem., Bull. Chem. Soc. (Jpn)* 42, 3505–08 (1969).

J. Moffatt and H. Khorana, *J. Am. Chem. Soc.,* 649–59 (1961).

B. Fischer, et al., *J. Med. Chem.* 36, 3937–46 (1993).

N. Kotchetkov, et al., *Tetrahedron Lett.* 1993 (1971).

J. Barrio, et al., *Biochem. Biophys. Res. Commun.* 46, 597 (1972).

J. Secrist, et al., *Biochemistry* 11, 3499 (1972).

J. Bierndt, et al., *Nucleic Acids Res.* 5, 789 (1978).

K. Koyasuga–Mikado, et al., *Chem. Pharm. Bull. (Tokyo)* 28, 932 (1980).

J. Ludwig and F. Eckstein, *J. Org. Chem.,* 54, 631–35 (1989).

G. Blackburn, et al., *J. Chem. Soc. Perkin Trans.,* I, 1119–25 (1984).

T. Myers, et al., *J. Am. Chem. Soc.* 85, 3292–95 (1963).

E. Rapaport, et al., *Proc. Nat. Acad. Sci. USA* 78, 838–42 (1981).

K. Ng and L.E. Orgel, *Nucleic Acids Res.* 15 (8) 3572–80 (1987).

L. Gheber, et al., *Membrane Biol.* 147, 83–93 (1995).

* cited by examiner

METHOD OF TREATING OTITIS MEDIA WITH URIDINE TRIPHOSPHATES AND RELATED COMPOUNDS

TECHNICAL FIELD

This invention relates to a method of removing or preventing the accumulation of retained mucous secretions from the middle ear of a patient by administering certain uridine, adenosine, or cytidine triphosphates.

BACKGROUND OF THE INVENTION

Otitis media (OM) is a viral or bacterial infection of the middle ear primarily, but not exclusively, afflicting children under three years of age. It is characterized by the presence of congested fluid in the middle ear and is usually precipitated by an infection in the respiratory tract which spreads into the middle ear via the nasopharnyx and eustachian tube. The incidence of OM is increasing—annual physician's office visits for OM have increased 150% from 1975 through 1990 (L. McCraig and J. Hughes, JAMA 273(3), 214–19 (1995)). This is most likely due to increased use of large-group day care facilities, where children are exposed to more respiratory pathogens. Approximately 25–40 million office visits are made each year for diagnosis and treatment of OM, and by age three, approximately 75% of children will have had at least one episode of acute OM (with the maximum incidence in children 6–24 months of age) (J. Klein, Clin Infect Dis 19, 823–33 (1994)). Anatomically, the eustachian tubes in infants are shorter, wider, and lie more horizontally than in older children and adults, facilitating the spread of pathogens from the nasopharnyx to the middle ear (L. Schwartz and R. Brown, Arch Intern Med 152, 2301–04 (1992)). The infection evokes an inflammatory response in the mucosal tissue of the eustachian tube and middle ear, resulting in fluid effusion in the middle ear. The resulting fluid is viscous and pus-filled, making normal mucociliary movement of the fluid difficult, and inflammation of the eustachian tube at its narrowest point, the isthmus, effectively blocks drainage of the fluid into the nasopharnyx (J. Klein, supra (1994)). Middle ear congestion can be expected to cause significant pain, dizziness, and hearing impairment in the patient; the average hearing loss from the fluid accumulation is 25 decibels. This is of particular concern in very young children because impairment of hearing could delay or seriously impede aspects of normal cognitive development which are dependent upon exposure to language and social interaction (D. Teele, et al. J. Infect Dis 1621, 685–94 (1990)). Other potential (but uncommon) sequelae of OM include mastoiditis, meningitis, extradural abscess, subdural empyema, brain abscess, and lateral sinus thrombosis.

About 80–90% of OM effusions eventually resolve spontaneously following antibiotic therapy; the process may take as long as three months. However, congestion in the middle ear may persist for weeks or even months beyond sterilization of this fluid with antibiotics due to a continued hypersecretory state of the mucous-producing cells. (S. Wintermeyer and M. Nahata, Annals of Pharmocotherapy 28, 1089–99 (1994)). The cause of this persistent hypersecretory state is not well understood but may relate to unrelieved underlying eustacan tube obstruction. As a further impediment to treatment, the effectiveness of antibiotic therapy is decreasing on account of growing bacterial resistance to antibiotics (M. Poole, Pediatr Infect Dis J. 14(4), 523–26 (1995)). If middle ear congestion persists for more than three months, surgery is commonly performed to insert a typanostomy tube to ventilate the middle ear of the patient (K. Grundfast, Arch Otolaryngol Head Neck Surg, 120, 797–98 (1994)). Tympanostomy surgery is now the second most frequent surgical procedure in children (after circumcision) (J. Klein, supra (1994)). The tube allows drainage of the fluid out of the ear and eventual resolution of the disease in a vast majority of chronic cases. However, the surgery is costly (>$2,000), and requires administering general anesthesia, a particular concern in infant patients. Furthermore, potential (but uncommon) sequelae of the surgery include persistent otorrhea, permanent perforation or scarring of the tympanic membrane, and cholesteatoma (a cyst-like sac filled with keratin debris that can occlude the middle ear and erode surrounding structures) (J. Klein, supra (1995)).

Thus, as a result of the decreasing effectiveness of antibiotic therapy due to bacterial resistance and the high costs and risks associated with typanostomy surgery, medical researchers have sought to develop other effective therapies for this increasingly prevalent disease. A French biotechnology company, Laboratoires SYNTHELABO FRANCE, has developed a method of treating nasal mucous fluid congestion under the trademark name rhinATP™ which uses adenosine triphosphate (ATP) as the active compound. This technology was licensed under U.S. Pat. No. 5,420,116 (applicant intends the disclosure of this and all other patent references and publications cited herein be incorporated herein by reference). Their method of treatment comprises administering ATP to the nasal cavity via nasal spray or nasal drops. Uridine triphosphate (UTP) and adenine triphosphate (ATP) have also been shown to effect the ion transport activity of human airway epithelial cells, as described in U.S. Pat. No. 5,292,498. Specifically, UTP and ATP induce chloride and water secretion by the lung epithelial cells of cystic fibrosis patients, helping to liquify and facilitate transport of the highly viscous airway surface mucus that characterizes this disease. It has also been found that UTP and ATP stimulate the ciliary beat frequency in lung epithelial cells, further facilitating the transport of mucus from the lungs of cystic fibrosis patients. See, R. Boucher, et al., Adenosine and Adenine Nucleotides: From Molecular Biology to Integrative Physiology, p. 525–532 entitled "Mechanisms and Therapeutic Actions of Uridine Triphosphates in the Lung" (L. Belardinelli, et al. ed., Alumwer Academic Publishers, Boston 1995); see also, L. Gheber, et al., J. Membrane Biol. 147, 83–93 (1995). Applicant has discovered that the high viscosity of the retained middle ear fluid in OM patients can be alleviated by administering UTP and its related compounds, as well as other nucleoside phosphates such as: adenosine 5'-triphosphate (ATP); cytidine 5'-triphosphate (CTP); 1,$N^6$-ethenoadosine triphosphate; adenosine 1-oxide triphosphate; 3,$N^4$-ethenocytidine triphosphate; $P^1,P^4$-di(adenosine-5') tetraphosphate ($A_2P_4$); or $P^1,P^4$-di(uridine5') tetraphosphate ($U_2P_4$) to the site of fluid blockage.

SUMMARY OF THE INVENTION

A method of treating otitis media in a subject in need of such treatment is disclosed. The method comprises administering to the middle ear of the subject a compound of Formula I, or a pharmaceutically acceptable salt thereof, in an amount effective to promote fluid drainage from the middle ear by hydrating mucous secretions in the middle ear and by increasing ciliary beat frequency in the middle ear and eustachian tube:

Formula I

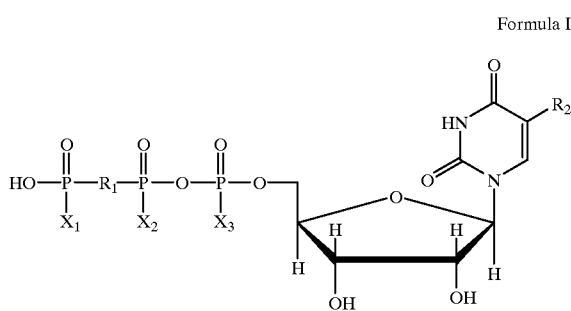

wherein:

$X_1$, $X_2$, and $X_3$ are each independently either $O^-$ or $S^-$. Preferably, $X_2$ and $X_3$ are $O^-$.

$R_1$ is O, imido, methylene, or dihalomethylene (e.g., dichloromethylene, diflouromethylene). Preferably, $R_1$ is oxygen or difluoromethylene.

$R_2$ is H or Br. Preferably, $R_2$ is H. Particularly preferred compounds of Formula I are uridine 5'-triphosphate (UTP) and uridine 5'-O-(3-thiotriphosphate) (UTPγS).

Formula I is the preferred embodiment of the compound, however, the method of the present invention can also include administering a compound of Formula II (adenosine 5' triphosphate [ATP] or 1,$N^6$-ethenoadenosine triphosphate or adenosine 1-oxide triphosphate), or Formula III (cytidine 5' triphosphate [CTP] or 3,$N^4$-ethenocytidine triphosphate), or Formula IV ($P^1,P^4$-di(adenosine-5') tetraphosphate ($A_2P_4$) or $P_1,P_4$ di(uridine-5') tetraphosphate ($U_2P_4$).

Formula II

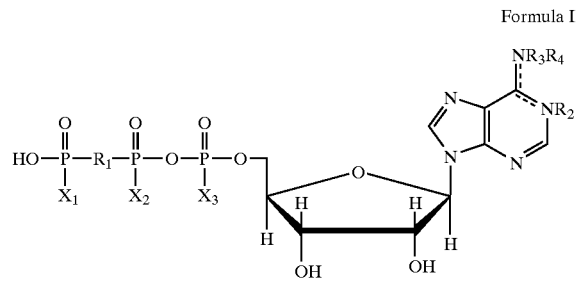

wherein:

$R_1$, $X_1$, $X_2$, and $X_3$ are defined as in Formula I.

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$ and $R_2$ taken together are —CH=CH—, forming a ring from N-6 to N-1 with a double bond between N-6 and C-6 (1,$N^6$-ethenoadenine).

Formula III

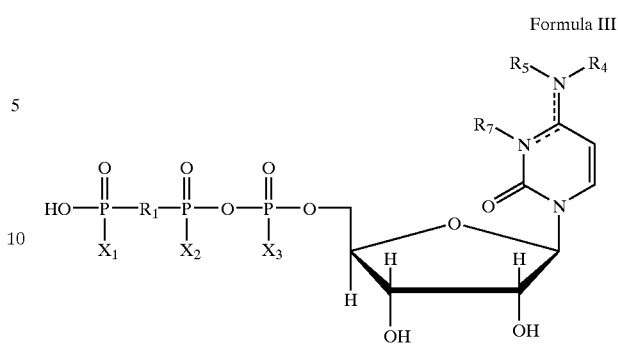

wherein:

$R_1$, $X_1$, $X_2$, and $X_3$ are defined as in Formula I.

$R_5$ and $R_6$ are H while $R_7$ is nothing and there is a double bond between N-3 and C-4 (cytosine), or, $R_5$, $R_6$ and $R_7$ taken together are —CH=CH—, forming a ring from N-3 to N-4 with a double bond between N-4 and C-4 (3,$N^4$-ethenocytosine).

Formula IV wherein:

B is adenine or uracil.

A second aspect of the present invention is a pharmaceutical formulation containing the compound of Formula I, II, III, or IV in an amount effective to promote fluid drainage from the middle ear by hydrating the mucous secretions in the middle ear and by increasing the ciliary beat frequency in the middle ear and eustachian tube, in a pharmaceutically acceptable carrier.

A third aspect of the present invention is the use of the active compounds disclosed herein for the manufacture of a medicament for the therapeutic hydration of mucous secretions in the middle ear and for the activation of ciliary beat frequency in the middle ear and eustachian tube of a patient in need of such treatment.

DESCRIPTION OF THE SPECIFIC EMBODIMENTS

The method of the present invention may be used to promote drainage of congested fluid from the middle and external ear of a subject in need of such treatment for any reason, including (but not limited to) retained secretions arising from middle and external ear diseases such as otitis media, acute otitis media, otitis media with persistent effusion, serous otitis media (arising from an unresolved acute infection, an allergic reaction, or barotrauma such as from rapid descent in an aircraft), or otitis externa. The method of the present invention may also be used to treat inner ear disease, including (but not limited to) Meniere's Disease. The present invention induces drainage of middle ear mucous secretions by hydrating the retained secretions and by increasing the ciliary beat frequency of cilia on the surface of the middle ear and eustachian tube. Hydration of the mucous secretions decreases their viscosity, allowing them to be more easily transported from the middle ear and eustachian tube to the nasopharnyx via mucociliary action. Additionally, the present invention accelerates this mucociliary action, further facilitating drainage of retained middle ear secretions into the nasopharnyx.

The present invention is concerned primarily with the treatment of human subjects, but may also be employed for the treatment of other mammalian subjects, such as dogs and cats, for veterinary purposes.

Compounds illustrative of the compounds of Formula I above include: (a) uridine 5'-triphosphate (UTP); (b) uridine 5'-O-(3-thiotriphosphate) (UTPγS); and (c) 5-bromo-uridine 5'-triphosphate (5-BrUTP). These compounds are known or may be made in accordance with known procedures, or variations thereof which will be apparent to those skilled in the art. See generally N. Cusack and S. Hourani, *Annals N.Y. Acad. Sci.* 603, 172–81 (entitled "Biological Actions of Extracellular ATP"). For example, UTP may be made in the manner described in Kenner, et al., *J. Chem. Soc.* 1954, 2288; or Hall and Khorana, *J. Am. Chem. Soc.* 76, 5056 (1954). See Merck Index, Monograph No. 9795 (11th Ed. 1989). UTPγS may be made in the manner described in R. S. Goody and F. Eckstein, *J. Am. Chem. Soc.* 93, 6252 (1971).

For simplicity, Formula I herein illustrates uridine triphosphate active compounds in the naturally occuring D configuration, but the present invention also encompasses compounds in the L configuration, and mixtures of compounds in the D and L configurations, unless otherwise specified. The naturally occuring D configuration is preferred.

Compounds illustrative of the compounds of Formula II above include (a) adenosine 5'-triphosphate (ATP) and (b) 1,$N^6$-ethenoadenosine triphosphate. Compounds illustrative of the compounds of Formula III above include (a) cytidine 5'-triphosphate and (b) 3,$N^4$-ethenocytidine triphosphate. These compounds can be made in accordance with known procedures, or variations thereof which will be apparent to those skilled in the art. For example, phosphorylation of nucleosides by standard methods such as D. Hoard and D. Ott, *J. Am. Chem. Soc.* 87, 1785–1788 (1965); M. Yoshikawa, et al., *Tetrahedron Lett.* 5065–68 (1967) and idem., *Bull. Chem. Soc. (Jpn)* 42, 3505–08 (1969); J. Moffatt and H. Khorana, *J. Am. Chem. Soc.* 83, 649–59 (1961); and B. Fischer, et al., *J. Med. Chem.* 36, 3937–46 (1993) and references therein. Etheno derivatives of cytidine and adenosine are prepared by known methods such as: N. Kotchetkov, et al., *Tetrahedron Lett.* 1993 (1971); J. Barrio, et al., *Biochem. Biophys. Res. Commun.* 46, 597 (1972); J. Secrist, et al., *Biochemistry* 11, 3499 (1972); J. Bierndt, et al., *Nucleic Acids Res.* 5, 789 (1978); K. Koyasuga-Mikado, et al., *Chem. Pharm. Bull. (Tokyo)* 28, 932 (1980). Derivatives with alpha, beta and gamma thiophosphorus groups can be derived by the following or by adapting methods of: J. Ludwig and F. Eckstein,*J. Org. Chem.* 54, 631–35 (1989); F. Eckstein and R. Goody, *Biochemistry* 15, 1685 (1976); R. Goody and F. Eckstein, *J. Am. Chem. Soc.* 93, 6252 (1971).

Compounds of Formulas I, II, or III where $R_1$ is $CCl_2$ and $CF_2$ can be prepared by methods similar to that described in G. Blackburn, et al.,*J. Chem. Soc. Perkin Trans. I,* 1119–25 (1984). Compounds of Formula I, II, III where $R_1$ is $CH_2$ can be prepared by methods similar to that described in T. Myers, et al., *J. Am. Chem. Soc.* 85, 3292–95 (1963).

Compounds illustrative of the compounds of Formula IV include ($P^1,P^4$-di(adenosine-5') tetraphosphate ($A_2P_4$) or $P^1,P^4$-di(uridine-5') tetraphosphate ($U_2P_4$). These compounds can be made in accordance with known procedures, or variations thereof which will be described by: P. Zamecnik, et al., *Proc. Natl. Acad. Sci. USA* 89, 838–42 (1981); and K. Ng and L. E. Orgel, *Nucleic Acids Res.* 15 (8), 3572–80 (1987).

In addition, UTP, ATP, CTP, $A_2P_4$, 3,$N^4$-ethenocytidine triphosphate, 1,$N^6$-ethenoadenine triphosphate, adenosine 1-oxide triphosphate, ATPγS, ATPβS, ATPαS, $AMPPCH_2P$, AMPPNHP, $N^4$-ethenocytidine and 1,$N^6$-ethenoadenosine are commercially available, for example, from Sigma Chemical Company, PO Box 14508, St. Louis, Mo. 63178.

The active compounds of Formulae I–IV may be administered by themselves or in the form of their pharmaceutically acceptable salts, e.g., an alkali metal salt such as sodium or potassium, an alkaline earth metal salts such as manganese, magnesium and calcium or an ammonium and tetraalkyl ammonium salts, $NX_4^+$ (wherein X is $C_{1-4}$). Pharmaceutically acceptable salts are salts that retain the desired biological activity of the parent compound and do not impart undesired toxicological effects.

The active compounds disclosed herein may be administered to the middle ear of a patient to promote fluid drainage in otitis media by a variety of suitable means, but are preferably administered by administering a liquid/liquid suspension (either a nasal spray of respirable particles which the subject inhales, or nasal drops of a liquid formulation) comprised of the active compound. Liquid pharmaceutical compositions of the active compound for producing a nasal spray or nasal drops may be prepared by combining the active compound with a suitable vehicle, such as sterile pyrogen free water or sterile saline by techniques known to those skilled in the art.

The dosage of active compound to promote fluid drainage will vary depending on the condition being treated and the state of the subject, but generally an effective amount is the amount sufficient to achieve concentrations of active compound on the middle ear surfaces of the subject of from about $10^{-7}$ to about $10^{-2}$ Moles/liter, and more preferable from about $10^{-6}$ to about $3\times10^{-4}$ Moles/liter.

Depending upon the solubility of the particular formulation of active compound administered, the daily dose to promote fluid drainage may be divided among one or several unit dose administrations. Preferably, the daily dose is no more than two times per day.

Another means of administering the active compound to the middle ear of the patient to promote fluid drainage may include any oral form of the active compound, administered to the patient either by means of a liquid suspension of the active compound which is poured into the mouth of the patient, or by means of a pill form swallowed by the patient.

Another means of administering an effective amount of the active compound to the middle and inner ear would involve the patient inhaling a nebulized form of the active compound into their respiratory tract, such that the active compound enters the nasopharnyx and subsequently enters the inner and middle ear of the patient.

Another means of administering the active compound to the middle ear would include any topical form of the active compound, administered as a cream or gel to the outer ear, which would subsequently permeate through the tympanic membrane into the middle ear of the patient.

Another means of administering the active compound to the middle ear would involve an injected form of the active compound, injected from the outer ear directly through the tympanic membrane into the middle ear, or injected indirectly through the upper neck region into the middle ear.

Another means of administering the active compound to the middle ear would involve a suppository form of the active compound, such that a therapeutically effective amount of the compound reaches the middle ear via systemic absorption.

An additional means of administering the active compound would involve intra-operative instillation of the active compound into the middle, inner or outer ear via a gel, cream, or liquid suspension form of the active compound, such that a therapeutically effective amount reaches the middle, inner or outer ear.

UTP and compounds of Formulae I–IV also have therapeutic benefit when used in combination with other agents used to treat otitis media, such as, but not limited to: antibiotics like penicillin, penicillan plus beta-lactam, erythromycin plus sulisoxazole, cephalosporin, trimethoprim, trimethoprim plus sulfamethoxazole, macrolides, and oxazolidinones; vaccines; antihistamines, decongestants, mucolytic agents; nonsteroidal antiinflammatory agents; and corticosteroids. UTP may also be used in combination with agents under development, such as NE-1530—a naturally occuring airway oligosaccharide (Neose Technologies, Inc.), and gene therapy.

The present invention is explained in greater detail in the Examples which follow. These examples are intended as illustrative of the invention, and are not to be taken as limiting thereof.

EXPERIMENTAL

Example 1

Treatment of Otitis

Uridine 5'-triphosphate (UTP) is administered to children diagnosed with otitis media (OM). UTP is administered via nasal drops or nasal spray, twice daily, for a total of 5–10 days. The concentration of UTP is in the range of $10^{-7}$ to $10^{-2}$ moles/liter. Treatment with UTP begins as soon as OM is diagnosed and antibiotic therapy is initiated. The length of treatment for each patient is up to one month (28 days); the preferable length of treatment is one week (7 days).

Effectiveness of UTP in eliminating middle ear fluid is assessed by several methods including: pneumatic otoscopy (to diagnose fluid in the middle ear and to evaluate the status of eardrum); tympanometry (to evaluate compliance of tympanic membrane/eardrum and to estimate middle ear pressure); acoustic reflectometry (to diagnose presence of air or fluid in the middle ear); and hearing evaluation tests.

The efficacy of UTP in treating otitis media is demonstrated by a decrease in the number of days that middle ear fluid is present and a decrease in the number of days that symptoms such as pain or hearing impairment are experienced by the patient.

The subject methods and compounds described herein provide a means for inducing drainage of middle ear secretions in a patient afflicted with otitis media. The method comprises administering to the middle ear of the subject a uridine triphosphate such as uridine 5'-triphosphate (UTP) or any analog of UTP in an amount effective to hydrate middle ear mucous secretions or stimulate ciliary beat frequency in the middle ear or eustachian tube.

The invention now being fully described, it will be apparent to one of ordinary skill in the art that many changes and modifications can be made thereto without departing from the spirit or scope of the appended claims.

What is claimed is:

1. A method of treating otitis media in a subject in need of such treatment, said method comprising administering to the subject a compound of Formula IV, or a pharmaceutically acceptable salt thereof, in a pharmaceutical carrier having an amount of said compound effective to promote fluid drainage from the middle ear, wherein the active ingredient is:

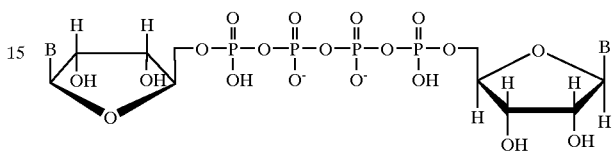

Formula IV wherein B is 1-uracilyl.

2. The method according to claim 1, wherein said compound is administered in an amount sufficient to achieve concentrations thereof on the middle ear or eustacian tube surfaces of said subject of from about $10^{-7}$ to about $10^{-2}$ Moles/liter.

3. The method according to claim 1, wherein said compound is delivered by administering a liquid/liquid suspension, including nasal drops or spray, of said compound to the nasopharngeal airways of said subject, such that a therapeutically effective amount of said compound contacts the eustachian tube or middle ear of said subject either directly or via systemic absorption and circulation.

4. The method according to claim 1, wherein said compound is delivered by administering an oral form of said compound to said subject, such that a therapeutically effective amount of said compound contacts the eustachian tube or middle ear of said subject via systemic absorption and circulation.

5. The method according to claim 1, wherein said compound is delivered by administering an aerosol suspension of said compound to the nasopharyngeal airways of said subject, such that a therapeutically effective amount of said compound contacts the eustachian tube or middle ear of said subject via systemic absorption and circulation.

6. A method according to claim 1, wherein said compound is delivered by administering a topical form of said compound to the tympanic membrane of said subject, such that a therapeutically effective amount of said compound contacts the eustachian tube or middle ear of said subject via absorption across the tympanic membrane.

7. A method according to claim 1, wherein said compound is delivered by administering an injected form of said compound, such that a therapeutically effective amount of said compound contacts the eustachian tube or middle ear of said subject via systemic absorption and circulation.

8. A method according to claim 1, wherein said compound is delivered by administering a suppository form of said compound, such that a therapeutically effective amount of said compound contacts the eustachian tube or middle ear of said subject via systemic absorption and circulation.

* * * * *